US 6,723,048 B2

(12) United States Patent
Fuller (10) Patent No.: US 6,723,048 B2
(45) Date of Patent: Apr. 20, 2004

(54) METHOD AND APPARATUS FOR NON-INVASIVE ANALYSIS OF BLOOD GLUCOSE

(75) Inventor: Milton E. Fuller, Reno, NV (US)

(73) Assignee: Pindi Products, Inc., Reno, NV (US)

( * ) Notice: Subject to any disclaimer, the term of this patent is extended or adjusted under 35 U.S.C. 154(b) by 0 days.

(21) Appl. No.: 10/169,278

(22) PCT Filed: Dec. 28, 2000

(86) PCT No.: PCT/US00/35554

§ 371 (c)(1),
(2), (4) Date: Jun. 24, 2002

(87) PCT Pub. No.: WO01/47415

PCT Pub. Date: Jul. 5, 2001

(65) Prior Publication Data

US 2002/0193673 A1 Dec. 19, 2002

Related U.S. Application Data

(60) Provisional application No. 60/173,240, filed on Dec. 28, 1999, and provisional application No. 60/234,002, filed on Sep. 20, 2000.

(51) Int. Cl.[7] .............................. A61B 5/05; A61B 17/52; H01F 7/02

(52) U.S. Cl. ..................... 600/365; 600/407; 335/302

(58) Field of Search ................................ 600/365, 407, 600/409, 410, 9, 10, 345, 347; 335/302, 209, 306; 340/854.6; 361/182; 607/101

(56) References Cited

U.S. PATENT DOCUMENTS

| | | | | | |
|---|---|---|---|---|---|
| 5,411,023 A | * | 5/1995 | Morris et al. | ................ | 600/323 |
| 5,626,137 A | * | 5/1997 | Dumoulin et al. | .......... | 600/420 |
| 5,744,958 A | * | 4/1998 | Werne | .......... | 324/318 |
| 6,184,684 B1 | * | 2/2001 | Dumoulin et al. | .......... | 324/318 |
| 6,263,228 B1 | * | 7/2001 | Zhang et al. | ................ | 600/409 |
| 6,477,398 B1 | * | 11/2002 | Mills | .......... | 600/409 |

* cited by examiner

Primary Examiner—Max F. Hindenburg
Assistant Examiner—Navin Natnithithadha
(74) Attorney, Agent, or Firm—Pillsbury Winthrop LLP (57) ABSTRACT

An apparatus for non-invasive detection and quantitation of analytes in a sample, such as blood glucose, employs a novel amplifier that uses high-gauss permanent magnets to permit an Rf signal to be transmitted through the sample. The concentration of the analyte can be determined from the magnitude of the reduction in the amplitude of the Rf signal at a characteristic frequency.

57 Claims, 4 Drawing Sheets

METHOD AND APPARATUS FOR NON-INVASIVE ANALYSIS OF BLOOD GLUCOSE

PRIORITY CLAIM

This application is the National Phase of International Application PCT/US00/35554 filed Dec. 28, 2000 which designated the U.S. and that International Application was published under PCT Article 21(2) in English.

FIELD OF THE INVENTION

The present invention relates to an apparatus for noninvasive testing and monitoring of biological molecules such as glucose.

BACKGROUND OF THE INVENTION

Diabetes mellitus is a medical condition in which the body does not adequately produce the quantity or quality of insulin needed to maintain normal levels of glucose in the circulating blood. The two most common types of diabetes are type I, also known as Insulin Dependent Diabetes Mellitus (IDDM), which accounts for 5–10% of all cases, and type II or Non-Insulin Dependent Diabetes Mellitus (NIDDM), which accounts for 90–95% of all cases. IDDM occurs in childhood, and those suffering from the disease require insulin doses throughout their lives. NIDDM generally occurs in adults and, although insulin may be required, the disease may be controllable with oral medication, weight loss, a nutritious diet and a regular exercise program.

Diabetes affects about 16 million people in the U.S. and over 100 million people worldwide. Diabetes can lead to severe health complications associated with the accumulated affects of poor blood glucose control, including blindness, kidney failure, heart failure, and peripheral neuropathy associated with limb pain, poor circulation, gangrene and subsequent amputation (Davidson, *Diabetes Mellitus—Diagnosis and Treatment,* 3rd Edition, Churchill Livingstone, N.Y., 1991). As a result, frequent self-monitoring of blood glucose is crucial for effective treatment and for reducing diabetes-associated morbidity and mortality.

Currently glucose measurements are done by pricking a finger and extracting a drop of blood, which is applied to a test strip, causing a color reaction between blood glucose and chemicals on the test strip that can be analyzed by an optical meter (glucometer) to give a numerical glucose reading. However, the current glucose tests are painful, disrupt daily life, and may be difficult to perform in long term diabetic patients due to calluses on the fingers and poor circulation. As a result, the average diabetic patient tests his/her blood glucose levels less than twice a day, far fewer than the recommended 4–7 times a day, leading to poor blood glucose control.

A non-invasive glucose monitoring method that is fast, painless and convenient could provide adequate control and greatly reduce the complications commonly seen in diabetes patients and consequently reduce health care costs.

Several types of non-invasive glucose monitoring techniques have been proposed. These techniques measure glucose levels in blood, interstitial fluid, ocular fluids and sweat and include microdialysis, wick extraction, implanted electrochemical or competitive fluorescence sensors, extraction fluid techniques (iontophoresis, skin suction and suction effusion techniques) and optical techniques, such as near-infrared spectroscopy, infrared spectroscopy, Raman spectroscopy, photoacoustic spectroscopy, scatter and polarization changes.

Currently, the most actively studied non-invasive methods for blood glucose measurement are optical techniques. All are limited by low signal-to-noise ratios and poor reproducibility. Current instrumentation lacks specificity due to substantial chemical and physical interference.

Several patents have discussed the use of magnetic fields for the non-invasive detection of certain substances in the human body systems. In nuclear magnetic resonance (NMR), for example, permanent magnets have been used to create a first, or biasing magnetic field to align initially randomly oriented hydrogen protons present in the nuclei of a substance in the sample being tested. A second energy field is applied to increase the energy level of the nuclei. When the second energy field is allowed to collapse, the nuclei return to their original, unaligned state, releasing energy that is detected and analyzed in the form of an image or spectrum. Such spectra are characteristic of individual substances. As a result, NMR may be used to establish the presence and identity of such substances and the concentrations in which such substances are present.

French Patent No. 2,562,785 (Jeandey et al.) discusses a permanent magnet system for NMR imaging medical diagnostics using pole pieces separated by and bridging stacked permanent magnets to form an open examination area and electromagnetic coils to adjust the resulting magnetic field.

Japanese Patent No. 56-14145 (Nippon Denshi K. K.) discusses an arrangement of permanent magnets held within a cylinder. A spacer is placed within the cylinder and sandwiched about the spacer are a pair of cylindrical pole pieces having raised central portions that extend into the air gap between the pole pieces and from which the operative flux emanates.

U.S. Pat. Nos. 4,875,486 and 5,072,732 (Rappaport et al.) describe nuclear magnetic resonance apparatus for non-invasive blood glucose testing that includes a pair of opposed biasing permanent magnets, a surface coil apparatus mounted adjacent the biasing magnets, and an electronic circuit controlled by a microprocessor. The microprocessor activates an RF generator and a cyclically-operated gate, which excites the surface coil. The surface coil applies a second magnetic field, raising the energy state of glucose molecules in a patients finger and aligning their nuclei. The microprocessor then deactivates the RF generator, permitting the nuclei (dipoles) to relax and return to their original alignment, releasing energy that is detected by the surface coil and analyzed by the microprocessor. The process is repeated with a standard sample and the test results with the patient's finger are compared with the results obtained with the standard sample to determine the glucose concentration in the patient.

SUMMARY OF THE INVENTION

I have discovered a novel amplifier for substantially noise-free transmission of an Rf signal. Such an amplifier has many applications, including its use in apparatus for detection or quantitation of an analyte in a sample, such as a non-invasive glucose test apparatus for diabetic patients.

According to one embodiment of the invention, an amplifier is provided that comprises: (a) a plurality of spaced-apart permanent magnets that generate a magnetic field; (b) at least one transmission node, and at least one reflection node spaced apart from the transmission node with a gap therebetween, that are disposed within the magnetic field, the transmission and reflection nodes comprised of an electrically-conductive material; and (c) a source that generates an Rf signal having a selected frequency spectrum that is connected to the transmission node and reflection node, such that a detectable Rf signal is received by the reflection node. The magnets are preferably high-gauss magnets of grade 26 to grade 60, including but not limited to NdFeB magnets. As described below, permanent magnets of grade 36 to 41 have been used in apparatus for detection of glucose in a biological sample. For use in such apparatus, the transmission node and reflection node are preferably each in close proximity to one of the magnets to improve the Rf signal received by the reflection node. A magnetically permeable and electrically insulating barrier is optionally disposed between each node and said magnet in close proximity thereto to prevent contact between the nodes and magnets. An Rf source producing an Rf signal having a frequency of about 2 GHz to about 3 GHz has been successfully used in apparatus for detection of glucose, although other frequencies, or a broad spectrum of frequencies, may be used for other purposes. In order to analyze the Rf signal received by the reflection node, such an apparatus may further include an analyzer connected to the transmission node and the reflection node.

One embodiment of an apparatus that employs such an amplifier is an apparatus for detection or quantitation of an analyte in a sample, such as, for example, a biological sample such as a bodily fluid, tissue, or body part (e.g., a finger). For such purposes, the apparatus described above includes a space or receptacle between the transmission node and reflection node for receiving such a sample and an analyzer. An Rf signal having a magnitude at a characteristic frequency is detectable by the analyzer when the sample is placed in the space or receptacle, the magnitude at the characteristic frequency is reduced as a function of analyte concentration. Such an apparatus may be used, for example, for detection of a biological molecule, such as glucose, proteinaceous molecules and macromolecules (e.g., hemoglobins, virus particles, etc.), in a sample.

According to another embodiment of the invention, methods are provided for causing an Rf signal to be transmitted between spaced-apart transmission and reflection nodes. Such methods comprise: (a) providing at least one transmission node, and at least one reflection node spaced apart from the transmission node with a gap therebetween, the transmission and reflection nodes comprised of an electrically-conductive material, and, connected to the transmission node and a reflection node, a source that generates an Rf signal having a selected frequency spectrum; and (b) disposing the transmission node and the reflecting node in a magnetic field produced by a plurality of spaced-apart high gauss permanent magnets.

According to another embodiment of the invention, methods are provided for detecting an analyte in a sample comprising: (a) providing an apparatus comprising (i) a plurality of spaced-apart permanent magnets that generate a magnetic field; (ii) at least one transmission node, and at least one reflection node spaced apart from the transmission node with a gap therebetween, that are disposed within the magnetic field, the transmission and reflection nodes comprised of an electrically-conductive material; (iii) a source that generates an Rf signal having a selected frequency spectrum that is connected to the transmission node and reflection node; and (iv) an analyzer connected to the transmission node and reflection node; (b) disposing a sample comprising an analyte between the transmission node and reflection node; and (c) using the analyzer to detect a reduction in the amplitude of the Rf signal at a frequency that is characteristic of the presence of the analyte. In order to quantitate the concentration of the analyte in the sample, the method may further comprise (d) determining the reduction of the amplitude of the Rf signal at the frequency that is characteristic of the presence of the analyte, and (e) determining the concentration of the analyte on the basis of said reduction of the amplitude.

The foregoing and other features and advantages of the invention will become more apparent from the following detailed description and accompanying drawings.

DETAILED DESCRIPTION OF THE INVENTION

Amplifier

Figure 1:
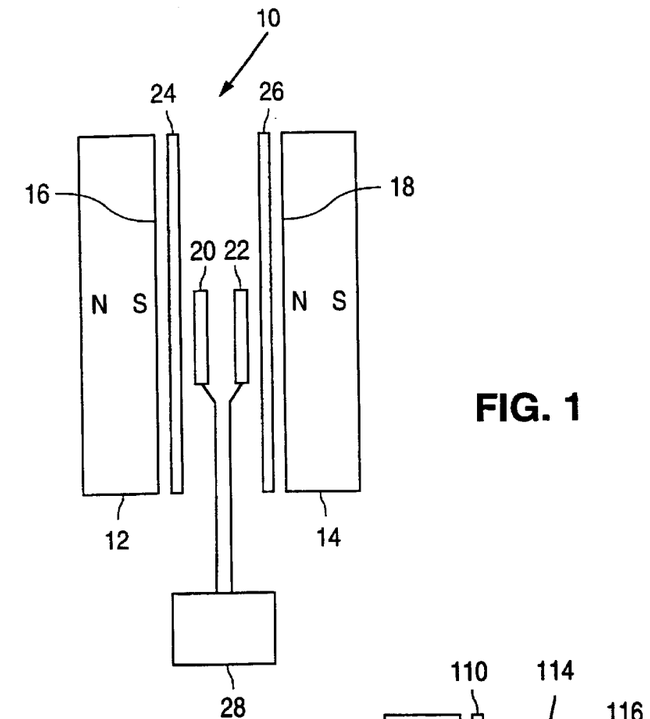
FIG. 1 is a schematic drawing of an amplifier according to the invention, with the north and south poles of the magnets oriented as shown.

I have discovered a novel amplifier design that employs an arrangement of two or more spaced apart high gauss permanent magnets oriented and aligned so as to create a single magnetic field. In FIG. 1, two spaced-apart high gauss permanent magnets 12, 14 are shown, although more than two permanent magnets may be used. Spaced-apart nodes or nodes 20, 22 comprising an electrically conductive material are positioned within the magnetic field created by the permanent magnets 12, 14, preferably between the magnets with each node 20, 22 in close proximity to a respective magnet 12, 14. In FIG. 1, two nodes are shown, a transmission node 20 and a reflection node 22, although multiple transmission nodes and/or reflection nodes may be used. As shown, the magnets are aligned such that poles of the magnets are at orthogonal to the alignment of the nodes 20, 22, with the north pole 16 of one magnet facing the south pole 18 of the other magnet. Barriers 24, 26 that are permeable to magnetic fields but that are electrically insulating are optionally positioned between the magnets and probes to permit a node to be in close proximity to a respective magnet while preventing direct contact. A source of an Rf signal 28 is connected to the nodes 20, 22.

High-gauss permanent magnets for use in connection with the amplifiers and apparatus of the present invention include magnets that are preferably about 26 grade to about 60 grade. The shape of the magnet is not critical. Bar magnets having a round or rectangular cross-section have been used successfully, for example, and. magnets having other shapes, such as disc, cylindrical, torus, etc., may also be used. In the glucose test apparatus described below, neodymium-iron-boron grade 39H/38H bar magnets are used that have a rectangular cross-section. Alternate embodiments employ a magnet of similar composition and strength having a round cross-section with a diameter of at least 0.4 inches and a length of at least 1.125 inches.

In operation, the magnetic field permits a detectable, substantially noise-free Rf signal to be received by the reflection node 22 that can be analyzed by an analyzer connected to the transmission mode 20 and reflection node 22 (not shown).

Apparatus for Non-Invasive Detection and/or Quantitation of an Analyte

Figure 2:
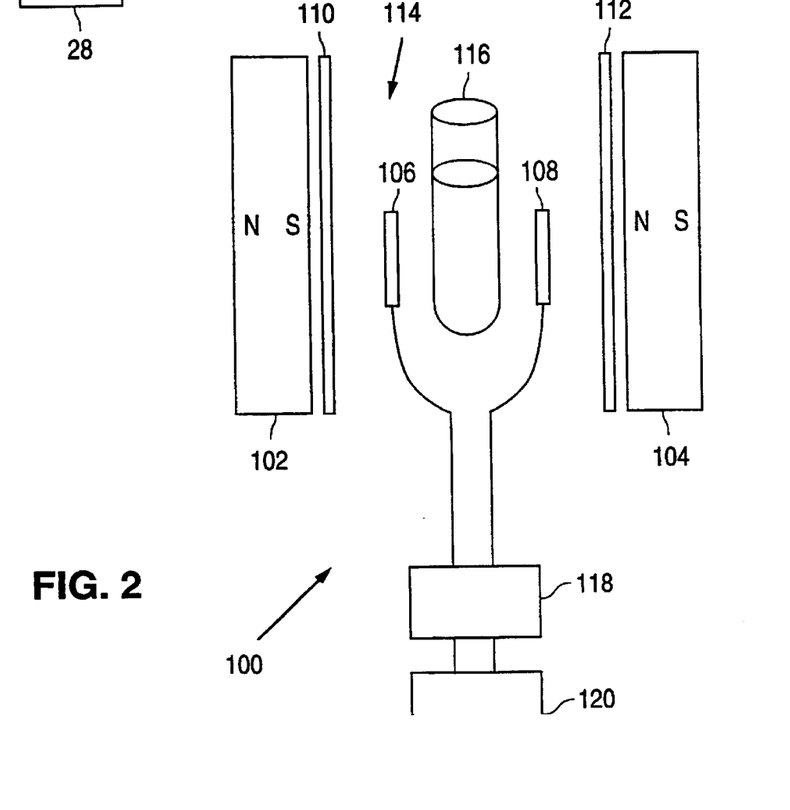
FIG. 2 is a schematic drawing of an embodiment of a non-invasive apparatus for detecting and/or quantitating an analyte in a sample according to the invention, with the north and south poles of the magnets oriented as shown.

According to another embodiment of the invention, an apparatus for non-invasive detection and/or quantitation of an analyte in a sample is provided that employs an amplifier as described above. Such an apparatus 100 is shown in schematic form in FIG. 2. Spaced apart high gauss permanent magnets 102, 104 are oriented so as to create a single magnetic field. Spaced-apart transmission and reflection nodes 106 and 108, respectively, are positioned in close proximity to, but not in contact with, the permanent magnets 102, 104 and within the magnetic field. Multiple transmission nodes and/or reflection nodes may be used. A non-electrically-conductive but magnetically permeable barrier 110, 112 separates each node from the closest magnet. The space or gap 114 defined between the nodes receives a sample 116 that comprises an analyte. As shown in FIG. 2, the sample 116 may consist of a cuvette, test tube or other vessel for holding an aqueous or non-aqueous fluid, gel, or solid sample, such as, for example, a body part (e.g., finger) or tissue of a patient, a body fluid such as blood, saliva, mucous, tears, intercellular fluid, etc., for analysis of analytes such as, for example, glucose, cholesterol, proteins such as hemoglobin Alc or hormones, viruses, and other target analytes.

An analyzer 118 and an Rf source 120 are connected to the nodes 106, 108. The Rf source 120 may produce a narrow frequency spectrum centered on a particular frequency that is selected to be appropriate for detection of a particular analyte. Such a frequency may readily be determined by experimentation. Alternatively, the Rf source may produce a wider frequency spectrum in order to permit the detection of multiple analytes in a single sample.

In operation, the sample 116 is placed or inserted between the transmission node 106 and reflection node 108 so as to be positioned between and in contact with or in close proximity to the nodes 106, 108. The magnetic field permits an Rf signal to be received by the reflection node 108. No Rf signal is detectable by the analyzer 118 in the absence of the magnetic field, as can be demonstrated by simply removing the magnets 102, 104 from the apparatus 100. The strength of the magnets 102, 104 (as measured in gauss units) must be sufficient to penetrate the sample 116 and to permit transmission of an Rf signal that is detectable by the analyzer 118. The analyzer 118 serves as a spectrum analyzer and measures the strength of the Rf signal (decibels, dB) as a function of frequency. The presence of the analyte in the tested sample 116 causes the amplitude of the Rf signal at the resonance frequency of the analyte to be reduced, and the magnitude of the reduction correlates with the concentration of the analyte in the sample. The orientation of the sample 116, e.g., a patient's finger, in the magnetic field is not critical.

Non-Invasive Blood Glucose Testing Apparatus

Figure 3:
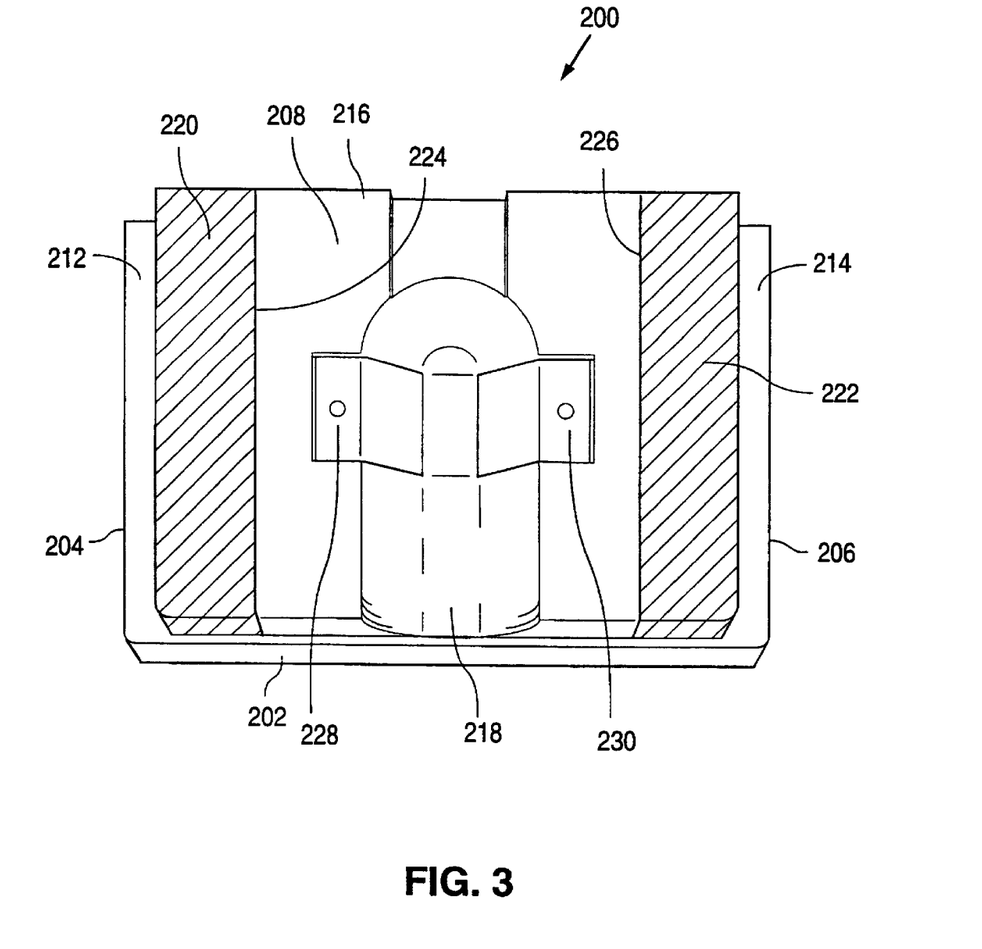
FIG. 3 is a top view of a glucose testing apparatus.
Figure 4:
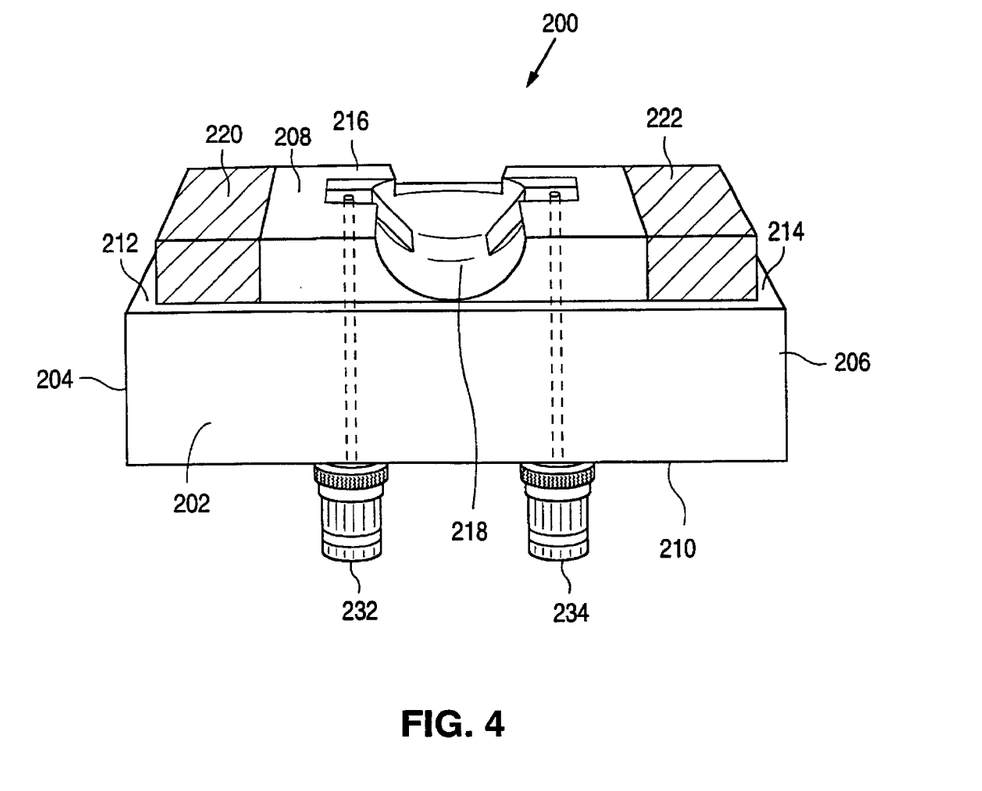
FIG. 4 is a side view of a glucose testing apparatus.
Figure 5:
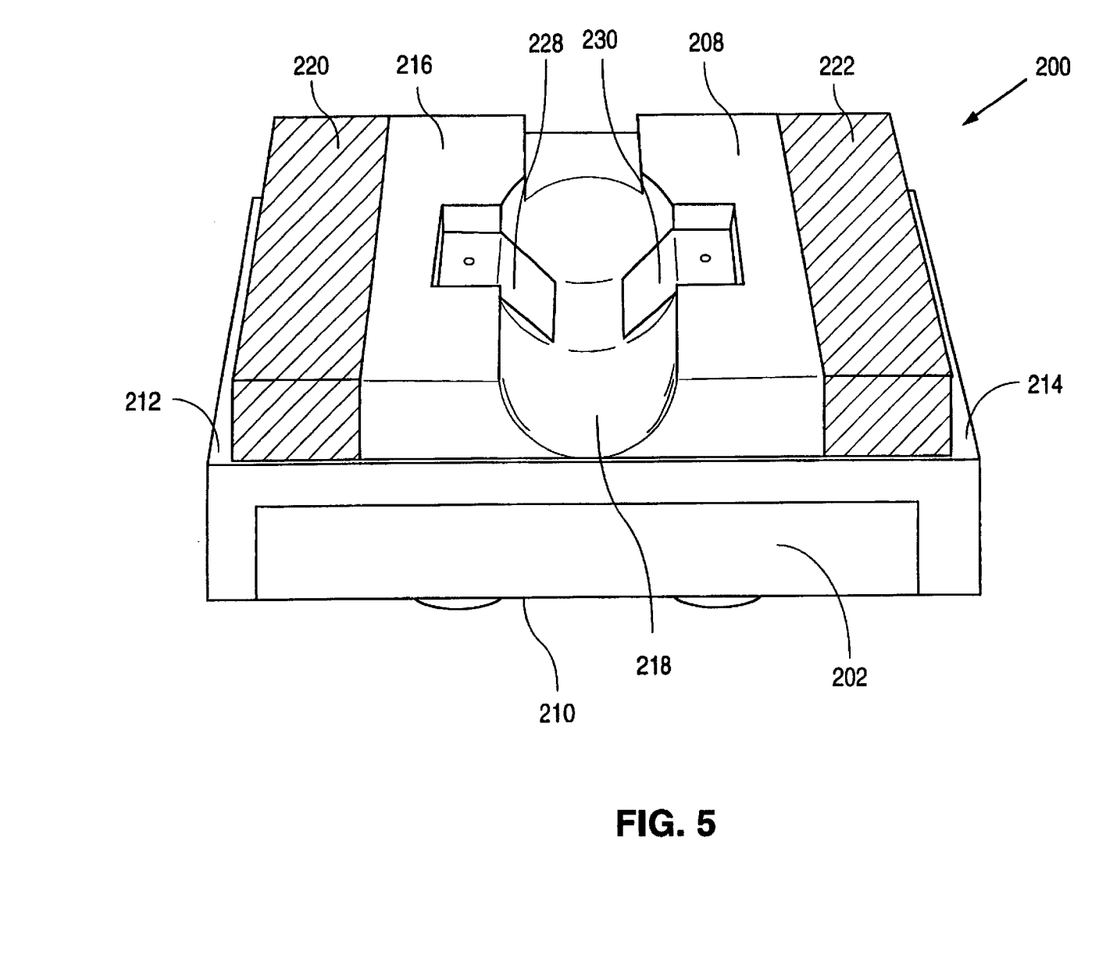
FIG. 5 is perspective view of a glucose testing apparatus.

One embodiment of an apparatus 200 for non-invasive glucose testing for diagnosis and monitoring of diabetes patients is shown in FIGS. 3, 4 and 5. This apparatus can also be used for detection and quantitation of other molecules, such as proteins and lipids, including, for example, P hemoglobin Alc (HbAlc). Such an apparatus can be small, lightweight, and portable, making is suitable for use in a doctor's office or at home. The non-invasive glucose test apparatus 200 shown in FIGS. 3–5 includes a body 202 made of a non-electrically-conductive material such as plastic (e.g., plexiglass) that includes a left edge 204, right edge 206, top surface 208 and bottom surface 210. The top surface 208 is shaped to define magnet inserts 212, 214 along the left edge 204 and right edge 206 and a raised central region 216 with a generally hemicylindrical finger insert 218 centrally located in the top surface of the central region 216 to receive a patient's finger. First and second spaced-apart neodymium-iron-boron grade 39 h/38 h anisotropic permanent magnets 220, 222 having a maximum energy product [BH]max[MGOe]=36.0–41.0 (N38H, Shin-Etsu Magnetics Inc., San Jose, Calif., USA) are situated in the magnet inserts 212, 214. As shown, the magnets 220, 222 are so oriented and aligned that the north pole 224 of first magnet 220 faces the south pole 226 of the second magnet 222 on either side of the central region 216. Opposed spaced-apart gold-plated copper transmission and reflection nodes 228, 230 extend into and along the surface of the insert 218 and are separated by an air space, such that a patient's finger (not shown) placed in the finger insert 218 contacts the nodes 228, 230. The nodes 228, 230 are connected to coaxial connectors 232, 234 that extend through the body 202 to extend away from the bottom surface of the body 210. A network analyzer (HP8722D, Hewlett-Packard Company, Palo Alto, Calif.) (not shown) that includes an Rf source, is connected to the connectors 232, 234.

In order to analyze a patient's glucose levels for diagnosing or monitoring diabetes, for example, the patient rests her finger in the finger insert 218 in contact with the transmission node 228 and reflection node 230 and within the magnetic field generated by the magnets 220, 222. The Rf out put from the network analyzer 236 is a signal (sine wave) having a frequency spectrum ranging from approximately 2 gigahertz (GHz) to approximately 3 GHz. The network analyzer 236 records the magnitude of the resulting Rf signal (measured in decibels, dB) as a function of frequency, which is then analyzed to determine the patient's blood glucose concentration. The change in the magnitude of the Rf signal at about 2.48 GHz correlates well with the concentration of glucose in the sample. Generally, about one second is required for a glucose reading using the apparatus 200.

Figure 6:
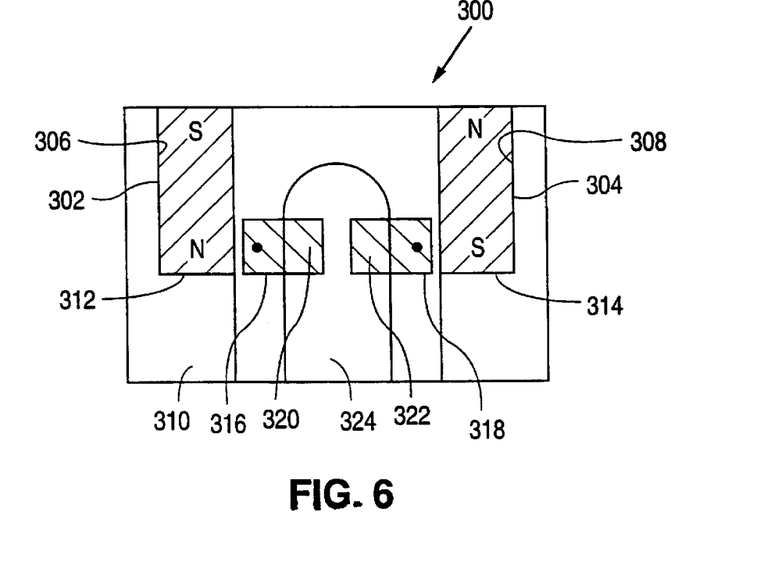
FIG. 6 is a top view of an alternative embodiment of the glucose testing apparatus, with the north and south poles of the magnets oriented as shown.

FIG. 6 shows a schematic top view of an alternate embodiment of the apparatus 300, which is generally similar to that shown in FIGS. 3–5. Permanent bar magnets 302, 304 having a circular cross-section are disposed in magnet inserts 306, 308 in the body 310 of the apparatus 300. The bottom edge 312, 314 of each of the magnets is aligned with the bottom edge 316, 318 of the transmission node 320 and the reflection node 322. The north-south axes of the magnets 302, 304 are aligned orthogonally to the alignment of the nodes 306, 308, which are spaced apart on opposite sides of the finger insert 324. This arrangement of the magnets with respect to the nodes stabilizes the magnetic field and improve signal transmission.

Data Analysis

The resulting data may be analyzed by any known method to determine blood glucose levels. In simplest terms, the glucose testing apparatus is used to test a group of non-diabetics who have fasted for an appropriate period, thereby generating a range of standardized wave pattern signals to determine the normal blood level in a standardized population. A patient is then tested after the same fasting period and the patient's wave pattern signals are compared to those of the standardized patterns. The comparison may be accomplished by visual comparison, although it is preferable for speed and reliability to employ computer analysis.

One method for analyzing such a signal is by fuzzy clustering, which can be summarized as follows. The preprocessed data for each spectrum obtained by testing a patient (sample spectrum) is transformed into a feature vector of 100 dimensions and written to a file. The feature vectors are then input to the fuzzy clustering program that partitions the vectors into groups, or clusters, that are similar. For a sufficiently large sample of spectral patterns (transformed into feature vectors), the range of glucose levels will be well represented, and each cluster will represent a portion of that range. Each cluster is represented by a prototypical feature vector that is determined by the clustering algorithm. After clustering a sufficiently large sample, K prototypes, or representative feature vectors, are used as standards that must be calibrated by the accompanying tests for actual blood glucose level as described below. After calibration, when a patient is observed with the glucose testing apparatus according to the present invention in order to obtain a spectrum, the spectrum is processed the same way as the sample spectra and a feature vector is obtained for that patient. This feature vector is then used to derive the blood sugar level of the patient.

First, to calibrate the prototypical feature vectors for each group or cluster of samples, it is necessary to know the actual blood glucose level of the patients from which the samples are obtained. The sample spectra and sample blood glucose levels must be taken very close together in time so as to minimize changes in the blood glucose levels. The set of all feature vectors obtained is clustered by means of a fuzzy clustering algorithm. A number K of clusters is obtained. For each cluster, the modified weighted fuzzy average (MWFEV) is taken of that cluster componentwise to obtain a prototype, or typical feature vector, for that cluster. The actual blood glucose levels for each patient whose feature vector falls into that cluster are averaged in the same manner to obtain the MWFEV of the blood glucose level. This MWFEV blood glucose level is, then, the blood glucose level for any patient with that particular feature vector as derived from that patient's spectrum. For each cluster there is a prototypical feature vector and a blood glucose level that represents it and thus calibrates it. The set of all feature vectors and their associated blood glucose levels are used to determine the blood glucose level of any patient who is later tested.

For a given patient, a spectrum is obtained using the glucose testing apparatus. The spectrum is then transformed into a feature vector that is compared to the prototypes. The two or three nearest prototypes are found and their blood glucose levels are read from a data table stored on a computer. Suppose that the three prototypes that are the closest to the feature vector of the patient are associated with the blood glucose levels of $g_1$, $g_2$, and $g_3$. Suppose further that the distances (Euclidian, mean-square, Mahalanobis, or other) of the patient's feature vector from the three prototypical feature vectors are $d_1$, $d_2$, and $d_3$. The blood glucose level of the patient is determined by taking a convex combination to interpolate from the three glucose levels via $$g = \alpha g_1 + \beta g_2 + \gamma g_3 \quad (1)$$

where $$\alpha = d_1/(d_1+d_2+d_3), \alpha = d_2/(d_1+d_2+d_3), \gamma = d_3/(d_1+d_2+d_3) \quad (2)$$

If, for example, the feature vector of the patient is closest to the first prototype, then $\alpha$ is larger than $\beta$ or $\gamma$, so the blood glucose for the first prototype has greater influence. This type of interpolation is very accurate if the prototypes are calibrated accurately. Two prototypes are required.

Next, a particular spectrum is converted into a feature vector. The spectrum file for a patient consists of a header, followed by 800 pairs of values (f, x) where f is a frequency and x is a magnitude value in decibels (positive and negative). The first 200 points and the last 200 points are not critical to the pattern, which depends essentially on the central 400 points. We read these central 400 points and record the second value (x) of each. Then we take the first four recorded decibel values, strip off the maximum value and the minimum value, and average the two remaining values to obtain an accurate representation of the 4-tuple of values. This $\alpha$-trimmed signal processing is well known. Because this process is symmetrical for positive and negative values, the process is valid over all points processed. Next, we take the following four values and do the same process on them. This continues until the 400 central decibel values have been exhausted. The resulting 100 representative values have the same shape as the central part of the original spectrum. This reduction of the dimension for the feature vectors provides compressed spectra and increases the speed of the process.

The 100 representative values for each sample spectrum are saved as a 100-dimensional vector to a file of feature vectors, if there are Q samples, then the completed file will contain Q such feature vectors. Once this file is complete, we process it with our fuzzy clustering algorithm to cluster the feature vectors into a number K of groups that is natural (the feature vectors in eRfh group are most alike in that their distance apart is relatively small compared to feature vectors in other groups).

A simple version of this method is to use each feature vector and actual blood glucose level as a singleton cluster. Thus, we record the feature vectors for a substantial number of patients along with their actual blood sugar levels determined from blood tests. When a patient is tested with a glucose test apparatus according to the present invention, the resulting spectrum is converted to a feature vector. The most similar feature vectors from the stored database of case feature vectors are retrieved along with their actual blood glucose levels. If there are k similar case feature vectors, the distances between the feature vector of the patient and the feature vectors are represented by $d_k$, and the weights $\alpha_k$ are computed as described in equation (2). The blood glucose level for the patient is determined by the fuzzy weighting of equation (1). The larger the case base of stored feature vectors, the greater is the accuracy in the interpolation. In this simplest approach, we circumvent the need to calibrate the fuzzy prototypes for each cluster of feature vectors.

Having illustrated and described the principles of the present invention, it will be apparent to persons skilled in the art that the invention can be modified in arrangement and detail without departing from such principles. I claim all such modifications that are within the spirit and scope of the appended claims.

What is claimed is:

1. An apparatus for substantially noise-free transmission of an Rf signal comprising:

(a) a plurality of spaced-apart permanent magnets that generate a magnetic field;

(b) at least one transmission node, and at least one reflection node spaced apart from the transmission node with a gap therebetween, that are disposed within the magnetic field, the transmission and reflection nodes comprised of an electrically-conductive material;

(c) a source that generates an Rf signal having a selected frequency spectrum that is connected to the transmission node and reflection node, such that a detectable Rf signal is received by the reflection nodes;

(d) an analyzer connected to the transmission node and the reflection node that analyzes the Rf signal received by the reflection node; and, (e) a space between the transmission node and reflection node for receiving a sample comprising an analyte, such that an Rf signal having a magnitude at a characteristic frequency is detectable by the analyzer when the sample is placed in the space or receptacle, the magnitude at the characteristic frequency is reduced as a function of analyte concentration.

2. The apparatus of claim 1 wherein the permanent magnets are each grade 26 to grade 60 magnets.

3. The apparatus of claim 2 wherein the permanent magnets are each grade 36 to grade 41 magnets.

4. The apparatus of claim 2 wherein the permanent magnets are each NdFeB magnets.

5. The apparatus of claim 1 wherein the transmission node and reflection node are each in close proximity to one of the magnets.

6. The apparatus of claim 5 comprising a magnetically permeable and electrically insulating barrier disposed between each node and said magnet in close proximity thereto to prevent contact therebetween.

7. The apparatus of claim 1 wherein the source produces an Rf signal having a frequency of about 2 GHz to about 3 GHz.

8. The apparatus of claim 1 wherein the sample is a biological sample.

9. The apparatus of claim 8 wherein the sample is a bodily fluid, tissue, or body part.

10. The apparatus of claim 9 wherein the sample is a finger.

11. The apparatus of claim 1 wherein the analyte includes a biological molecule.

12. The apparatus of claim 11 wherein the analyte is glucose.

13. A method for detecting an analyte in a sample comprising:

(a) providing an apparatus comprising (i) a plurality of spaced-apart permanent magnets that generate a magnetic field; (ii) at least one transmission node, and at least one reflection node spaced apart from the transmission node with a gap therebetween, that are disposed within the magnetic field, the transmission and reflection nodes comprised of an electrically-conductive material; (iii) a source that generates an Rf signal having a selected frequency spectrum that is connected to the transmission node and reflection node; and (iv) an analyzer connected to the transmission node and reflection node;

(b) disposing a sample comprising an analyte between the transmission node and reflection node; and (c) using the analyzer to detect a reduction in the amplitude of the Rf signal at a frequency that is characteristic of the presence of the analyte.

14. The method of claim 13 further comprising (i) determining the reduction of the amplitude of the Rf signal at the frequency that is characteristic of the presence of the analyte, and (ii) determining the concentration of the analyte on the basis of said reduction of the amplitude.

15. An apparatus for substantially noise-free transmission of an Rf signal comprising:

(a) a plurality of spaced-apart permanent magnets that generate a magnetic field;

(b) at least one transmission node, and at least one reflection node spaced apart from the transmission node with a gap therebetween, that are disposed within the magnetic field, the transmission and reflection nodes comprised of an electrically-conductive material, wherein the transmission node and reflection node are each in close proximity to one of the magnets;

(c) a magnetically permeable and electrically insulating barrier disposed between each node and said magnet in close proximity thereto to prevent contact therebetween; and, (d) a source that generates an Rf signal having a selected frequency spectrum that is connected to the transmission node and reflection node, such that a detectable Rf signal is received by the reflection node.

16. The apparatus of claim 15 wherein the permanent magnets are each grade 26 to grade 60 magnets.

17. The apparatus of claim 16 wherein the permanent magnets are each grade 36 to grade 41 magnets.

18. The apparatus of claim 16 wherein the permanent magnets are each NdFeB magnets.

19. The apparatus of claim 15 wherein the source produces an Rf signal having a frequency of about 2 GHz to about 3 GHz.

20. The apparatus of claim 15 further comprising an analyzer connected to the transmission node and the reflection node that analyzes the RF signal received by the reflection node.

21. The apparatus of claim 20 further comprising a space between the transmission rode and reflection node for receiving a sample comprising an analyte, such that an Rf signal having a magnitude at a characteristic frequency is detectable by the analyzer when the sample is placed in the space or receptacle, the magnitude at the characteristic frequency is reduced as a function of analyte concentration.

22. The apparatus of claim 21 wherein the sample comprises a biological sample.

23. The apparatus of claim 22 wherein the sample comprises a bodily fluid, tissue, or body part.

24. The apparatus of claim 23 wherein the sample comprises a finger.

25. The apparatus of claim 21 wherein the analyte includes a biological molecule.

26. The apparatus of claim 25 wherein the analyte is glucose.

27. A detector, which comprises:

a base;

a body part receiver supported by the base;

a pair of nodes positioned at spaced apart locations in the body part receiver to contact a body part positioned in the body part receiver; and, a pair of permanent magnets supported by the base, one of said magnets being positioned adjacent one of said nodes, the other of said magnets being positioned adjacent the other of said nodes.

28. The detector as claimed in claim 27, wherein said body part receiver is sized to receive a human digit in contact with said nodes.

29. The detector as claimed in claim 28, wherein said human digit is a finger.

30. The detector as claimed in claim 27, including a magnetically permeable and electrically insulating barrier disposed between each node and said magnet adjacent thereto to prevent contact therebetween.

31. The detector as claimed in claim 27, wherein each node comprises an electrically conducting plate.

32. The detector as claimed in claim 31, wherein each node comprises a gold-plated copper plate.

33. The detector as claimed in claim 27, including a source that generates an Rf signal having a selected frequency spectrum that is coupled to each node.

34. The detector as claimed in claim 33, including an analyzer coupled to each node.

35. The detector as claimed in claim 27, wherein the detector is adapted to detect a characteristic.

36. The detector as claimed in claim 35, wherein the characteristic is an analyte concentration.

37. The detector as claimed in claim 36, wherein the analyte includes a biological molecule.

38. The detector as claimed in claim 36, wherein the analyte comprises glucose.

39. The detector as claimed in claim 36, wherein the analyte comprises a protein.

40. The detector as claimed in claim 36, wherein the analyte comprises hemoglobin Alc.

41. The detector as claimed in claim 36, wherein the analyte comprises a virus.

42. The detector as claimed in claim 36, wherein the analyte comprises an enzyme.

43. The detector as claimed in claim 36, wherein the analyte comprises cholesterol.

44. The detector as claimed in claim 27 wherein the permanent magnets are each grade 26 to grade 60 magnets.

45. The detector as claimed in claim 27 wherein the permanent magnets are each grade 36 to grade 41 magnets.

46. The detector as claimed in claim 27 wherein the permanent magnets are each NJFeB magnets.

47. A method of detecting a characteristic, which comprises:

positioning a body part in a magnetic field;

directing an RF signal having a selected frequency spectrum into said body part positioned in said magnetic field;

analyzing an RF signal received from said body part positioned in said magnetic field to detect a characteristic in said body part.

48. The method as claimed in claim 47, wherein said body part is a human digit.

49. The method as claimed in claim 48, wherein said human digit is a finger.

50. The method as claimed in claim 47, wherein said characteristic includes a concentration of an analyte.

51. The method as claimed in claim 50, wherein said analyte includes a biological molecule.

52. The method as claimed in claim 50, wherein the analyte comprises glucose.

53. The method as claimed in claim 50, wherein the analyte comprises a protein.

54. The method as claimed in claim 50, wherein the analyte comprises hemoglobin Alc.

55. The method as claimed in claim 50, wherein the analyte comprises a virus.

56. The method as claimed in claim 50, wherein the analyte comprises an enzyme.

57. The method as claimed in claim 50, wherein the analyte comprises cholesterol.

\* \* \* \* \*

UNITED STATES PATENT AND TRADEMARK OFFICE
CERTIFICATE OF CORRECTION

PATENT NO. : 6,723,048 B2
DATED : April 20, 2004
INVENTOR(S) : Milton A. Fuller

It is certified that error appears in the above-identified patent and that said Letters Patent is hereby corrected as shown below:

Column 8,
Line 67, change "nodes", insert -- node --.

Column 11,
Line 29, change "NJFeB", insert -- NdFeB --.

Signed and Sealed this

First Day of June, 2004

JON W. DUDAS
*Acting Director of the United States Patent and Trademark Office*